United States Patent [19]

Franz et al.

[11] Patent Number: 4,828,826

[45] Date of Patent: May 9, 1989

[54] COSMETIC FORMULATIONS WITH CARRIER-FREE IRON OXIDE PLATELETS

[75] Inventors: Klaus D. Franz, Kelkheim; Andrea Griessmann, Darmstadt; Gisela Lenz, Gross Gerau; Gernot Möschl, Weiterstadt, all of Fed. Rep. of Germany

[73] Assignee: Merck Patent Gesellschaft Mit Beschränkter Haftung, Darmstadt, Fed. Rep. of Germany

[21] Appl. No.: 111,833

[22] Filed: Oct. 22, 1987

[30] Foreign Application Priority Data

Oct. 23, 1986 [DE] Fed. Rep. of Germany ....... 3636075

[51] Int. Cl.$^4$ .............................................. A61K 7/021
[52] U.S. Cl. ........................................ 424/63; 424/64; 424/69; 106/418
[58] Field of Search ............................. 424/63, 64, 69; 428/363; 106/292, 299

[56] References Cited

U.S. PATENT DOCUMENTS

| | | | |
|---|---|---|---|
| 3,926,659 | 12/1975 | Bernhard et al. | 106/308 B |
| 3,951,679 | 4/1976 | Bernhard et al. | 424/63 |
| 4,146,403 | 3/1979 | Armanini | 428/363 |
| 4,509,988 | 4/1985 | Bernhard | 428/363 |
| 4,565,581 | 1/1986 | Bernhard | 428/363 |

FOREIGN PATENT DOCUMENTS 3001438  8/1981  Fed. Rep. of Germany ........ 424/63

Primary Examiner—Thurman K. Page
Assistant Examiner—P. Prater
Attorney, Agent, or Firm—Millen & White

[57] ABSTRACT

A cosmetic formulation comprising a cosmetically compatible adjuvant and particles of at least one colored pigment is improved by using as the colored pigment a synthetic platelet-shaped iron oxide pigment. The resulting pigment enables improved skin feel in cosmetic preparations.

12 Claims, No Drawings

COSMETIC FORMULATIONS WITH CARRIER-FREE IRON OXIDE PLATELETS

BACKGROUND OF THE INVENTION

The application relates to cosmetic formulations containing platelet-shaped colored gloss pigments.

In cosmetics, there is a need for effect pigments which impart to the formulations a metallic colored gloss and contain physiologically acceptable dyestuffs permitted in cosmetics. It is known that platelet-shaped pigments, such as, for example, the metal oxide/mica pigments described in German Patents and Patent Application Nos. 1,959,998, 2,244,298 and 2,313,331, can be used for this. These are thin mica platelets coated with iron oxide and, if appropriate, other metal oxides.

However, in addition to the colored gloss and the aesthetic effects achieved with this, the behavior of the formulation on the skin, the so-called "feeling", also plays a decisive role in cosmetic formulations. The known cosmetic pigments are still in need of improvement in this respect.

SUMMARY OF THE INVENTION

It is therefore an object of the invention to provide cosmetic pigments with improved skin feel and advantageous aesthetic effect.

Upon further study of the specification and appended claims, further objects and advantages of this invention will become apparent to those skilled in the art.

It has now been found, surprisingly, that when synthetic platelet-shaped iron oxides are used in cosmetic formulations, particularly skin-friendly pleasant preparations are obtained, and very advantageous aesthetic effects can also be achieved by the metallic colored gloss.

These objects have been satisfied by the provision of cosmetic formulations containing platelet-shaped colored gloss pigments, which are characterized in that they contain synthetic platelet-shaped iron oxide pigments.

DETAILED DISCUSSION

While the cosmetic pigments based on mica are prepared by precipitating iron oxide and, if appropriate, other oxides as a thin layer onto the mica platelets, the iron oxides used according to the present invention are not applied to a platelet-shaped carrier but are themselves in the form of platelet-shaped crystals. They are therefore considerably thinner than the mica-based pigments and impart a considerably higher colored gloss, based on the weight of the pigment added, to the cosmetic formulations.

Again in contrast to the mica pigments, in which numerous tiny metal oxide crystals are deposited side by side on the mica surface and which therefore have, viewed under a microscope, a relatively rough surface, the pigments used in the formulations according to the invention are present as monocrystals which have a very smooth surface. As a result of these properties, the pigments have not only a high refractive index and high gloss but also a very good skin feeling.

The pigments used according to the invention are known per se and have also already been proposed for pigmenting anticorrosion and decorative coatings with a pronounced metallic gloss, both lacquers and enamels, glazes, plastics or synthetic resins being suitable as the coating material. The pigments are as a rule prepared by hydrothermal processes. Processes for their preparation are described, for example, in U.S. Pat. No. 2,989,411, European Patent No. 14,382, European Patent Application Nos. 1,180,881 and 68,311, German patent Specification No. 3,019,404 and other publications quoted in the patent rights mentioned. As well as pure iron oxides, mixed oxides which contain, for example, oxides of elements of main group and/or sub-group II, IV, V and/or VI of the periodic table of the elements or, for example, aluminum, are also described therein. The reduction of these pigments to magnetite or other mixed oxides of divalent iron and, if appropriate, reoxidation to maghaemite ($\gamma-Fe_2O_3$) is also known. All these synthetic platelet-shaped iron oxides are suitable for the formulations according to the invention.

The pigments as a rule have a diameter of the order of about 1 to about 50 $\mu$m and a thickness of about 0.1 to about 1 $\mu$m. particles of about 5 to about 20 $\mu$m in diameter are particularly preferred.

Because of the good gloss and the low weight of the platelets, only relatively small amounts of the pigments are required. Although the absolute amount depends on the nature of the formulation and the desired colored effect, as a rule about 6 to about 40% by weight of the pigments are employed.

Bases used for the formulations according to the invention are the substances customary for, for example, lipsticks, grease sticks, creams, powders and other cosmetics. These are known to the expert or are to be found in standard works, such as, for example, H. Janistyn, Handbuch der Kosmetika und Riechstoffe (Handbook of Cosmetics and Perfumes), Hüthig Verlag Heidelberg.

The formulations according to the invention contain as coloring constituents in all cases at least one of the abovementioned synthetic platelet-shaped iron oxides. In addition, however, other pigments can be admixed, it being possible to use both organic and inorganic absorption colored pigments, silver gloss pigments, such as, for example, bismuth oxychloride, pearl essence or titanium dioxide-coated mica, or interference colored gloss pigments based on mica platelets coated with metal oxides, in particular $TiO_2$. In combination with other pigments the platelet-shaped iron oxide pigments can make for 1–99%, preferably 20–80% by weight, of the total pigment content of the cosmetic composition.

Very attractive colored effects are achieved, in particular, by combination with interference colored pigments or metallic gloss pigments, so that these combinations are preferred. The present invention therefor provides very advantageous new cosmetic formulations with very attractive colored effects and a very pleasant skin feeling.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLE 1

Crayon cosmetic stick

A greasy phase, melted at 80° C. and consisting of: 40 parts by weight of Cutina LM (lipstick base from Henkel KGaA, Düsseldorf) and 20 parts by weight of paraffin are mixed with 40 parts by weight of a platelet-shaped red-brown glossy pigment which has been prepared according to Example 2 of U.S. Pat. No. 2,989,411, if appropriate perfume is added and the mixture is shaped to leads for cosmetic sticks by casting or extrusion and allowed to cool.

EXAMPLE 2

Cream mascara consisting of the following constituents:
10 parts by weight of stearic acid;
3.3 parts by weight of isopropyl myristate;
4.7 parts by weight of spermaceti;
1.0 part by weight of sorbitan monooleate;
1.0 part by weight of ethoxylated sorbitan fatty acid ester;
0.2 part by weight of propylparaben;
3.3 parts by weight of triethanolamine;
10.0 parts by weight of magnesium aluminium silicate;
7.5 parts by weight of Carboset 514 (acrylic resin from Goodrich, Cleveland);
2.5 parts by weight of propylene glycol;
0.1 part by weight of paraben;
46.4 parts by weight of demineralized water;
10 parts by weight of platelet-shaped $Fe_3O_4$, prepared according to Example 7 of European Patent Specification No. 14,382.

The constituents of the greasy phase and those of the aqueous phase are heated separately to about 75° C. and the aqueous phase is introduced slowly into the greasy phase, with stirring. After cooling, the emulsion is homogenized and the black pigment is stirred in. A mascara which imparts a silky shimmer to the eyelashes is obtained.

EXAMPLE 3

Loose face powder consisting of the constituents: 59 parts by weight of talc;
5 parts by weight of magnesium stearate;
10 parts by weight of finely divided mica platelets;
15 parts by weight of Timiron Super Sparkle MP-148 (nacreous pigment based on mica flakes coated with metal oxides, consisting of 86% by weight of mica and 14% by weight of $TiO_2$);
6 parts by weight of a red-brown platelet-shaped $Fe_2O_3$ pigment prepared by the process described in Journal of Colloid and Interface Science 74 (2) page 405 (1980); and
5 parts by weight of a binder consisting of 90 parts by weight of isopropyl stearate, 5 parts by weight of vaseline and 5 parts by weight of spermaceti.
If desired, perfume and preservatives.

The powder constituents are mixed homogeneously, the nacreous pigment and the iron oxide pigment are stirred in thoroughly and the mixture is then sprayed with the molten, thoroughly mixed binder. A delicate powder which has a velvety shimmer combined with an additional glitter effect and imparts a pleasant skin feeling is obtained.

EXAMPLE 4

Compact powder consisting of the following constituents:
49.5 parts by weight of talc;
7.5 parts by weight of potato starch;
2.5 parts by weight of magnesium stearate;
20 parts by weight of Timiron Super Violet (metal oxide mica pigment containing 51% by weight of mica and 49% by weight of $TiO_2$);
10 parts by weight of a platelet-shaped magnetite pigment prepared in accordance with Japanese Preliminary Published Specification No. 28,700/1976; and
10.5 parts by weight of a binder consisting of 85 parts by weight of isopropyl stearate, 5 parts by weight of spermaceti, 5 parts by weight of vaseline, 4 parts by weight of perfume oil and 1 part by weight of propylparaben.

The dry powder constituents are mixed homogeneously and sprayed with the molten and thoroughly mixed binder, with further mixing. The mixture is then pressed under a pressing pressure of 40-60 bar. An eyeshadow powder with a mellow metallic gloss and a soft skin feeling is obtained.

EXAMPLE 5

Lipstick with the following composition:
69 parts by weight of a base of the following composition:
3.85 parts by weight of castor oil;
2.50 parts by weight of beeswax;
8.00 parts by weight of isopropyl myristate;
7.50 parts by weight of carnauba wax;
5.00 parts by weight of lanolin;
3.00 parts by weight of heavy liquid paraffin;
0.10 part by weight of propylparaben;
0.05 part by weight of Oxynex 2004 (antioxidant from E. Merck, Darmstadt);
15 parts by weight of a colored paste of organic/inorganic dyestuffs in castor oil from Siegle-BASF, Stuttgart;
10 parts by weight of a violet platelet-shaped iron oxide pigment prepared according to Example 5 of European Pat. No. 68,311;
6 parts by weight of castor oil: and if desired, perfume.

The constituents of the base are heated to about 80° C. and mixed thoroughly. In a separate operation, the constituents of the colored paste are mixed to a paste in castor oil, being warmed to 60° C., and are passed over a roll mill once or twice for homogenization. The base, additional castor oil, the colored paste and the iron oxide pigment are then mixed in a casting apparatus, heated to about 60° C. and subsequently perfumed. The homogeneous melt is poured into a casting mold preheated to 60° C. and allowed to cool. The castings are removed from the molds cold and, after warming to room temperature, are flame treated again briefly. The sticks produce a uniform metallic colored shimmer on the skin.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a cosmetic formulation comprising a cosmetically compatible adjuvant and particles of at least one colored pigment, the improvement wherein at least one colored pigment is a synthetic platelet-shaped iron oxide pigment, wherein the iron oxide is carrier-free and whereby the cosmetic formulation has an improved skin feel.

2. A cosmetic formulation of claim 1, wherein the amount of iron oxide is effective to improve the skin feel thereof.

3. A cosmetic formulation of claim 2, wherein the iron oxide platelet has a smooth surface.

4. A cosmetic formulation according to claim 1, wherein the synthetic platelet-shaped iron oxide pigment is present in an amount of about 6–40% by weight based on the total formulation.

5. A cosmetic formulation according to claim 1, wherein the iron oxide is magnetite.

6. A cosmetic formulation according to claim 1, wherein the iron oxide is $Fe_2O_3$.

7. A cosmetic formulation according to claim 1, wherein the iron oxide additionally contains a group II, IV, V or VI metal oxide or a mixture thereof.

8. A cosmetic formulation according to claim 1, wherein the synthetic platelet-shaped iron oxide pigment particles have a diameter of about 1–50 µm and a thickness of about 0.1–1 µm.

9. A cosmetic formulation according to claim 1, wherein the synthetic platelet-shaped iron oxide particles have a diameter of about 5–20 µm.

10. A cosmetic formulation according to claim 1, wherein at least one colored pigment is a nacreous pigment comprising mica coated with at least one metal oxide.

11. A cosmetic formulation according to claim 10 wherein the nacreous pigment is mica coated with titanium dioxide.

12. A method of improving the skin feel of a cosmetic formulation comprising incorporating thereon an amount of synthetic carrier free platelet-shaped iron oxide pigment effective therefor.

* * * * *